(12) United States Patent
Zhao et al.

(10) Patent No.: US 9,878,506 B2
(45) Date of Patent: Jan. 30, 2018

(54) COMPLIANT YET TOUGH HYDROGEL SYSTEMS AS ULTRASOUND TRANSMISSION AGENTS

(71) Applicant: Massachusetts Institute of Technology, Cambridge, MA (US)

(72) Inventors: Xuanhe Zhao, Allston, MA (US); Shaoting Lin, Cambridge, MA (US); Hyunwoo Yuk, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/970,704

(22) Filed: Dec. 16, 2015

(65) Prior Publication Data

US 2016/0176128 A1 Jun. 23, 2016

Related U.S. Application Data

(60) Provisional application No. 62/095,243, filed on Dec. 22, 2014.

(51) Int. Cl.
| | |
|---|---|
| *A61K 9/00* | (2006.01) |
| *B29C 71/00* | (2006.01) |
| *A61K 49/22* | (2006.01) |
| *A61B 8/00* | (2006.01) |
| *C08J 3/075* | (2006.01) |
| *C08J 3/24* | (2006.01) |
| *B29K 105/00* | (2006.01) |
| *A61B 17/225* | (2006.01) |

(52) U.S. Cl.
CPC ........ *B29C 71/0009* (2013.01); *A61B 8/4281* (2013.01); *A61K 49/226* (2013.01); *C08J 3/075* (2013.01); *C08J 3/246* (2013.01); *A61B 2017/2253* (2013.01); *B29K 2105/0061* (2013.01); *B29K 2995/0078* (2013.01); *C08J 2300/14* (2013.01); *C08J 2300/208* (2013.01); *C08J 2333/26* (2013.01)

(58) Field of Classification Search
CPC .................................................. A61K 49/226
See application file for complete search history.

(56) References Cited

U.S. PATENT DOCUMENTS

2010/0055184 A1    3/2010 Zeitels

FOREIGN PATENT DOCUMENTS

| CN | 104311841 A | 1/2015 |
| WO | 2013/103856 A1 | 7/2013 |
| WO | 2013103956 A1 | 7/2013 |

OTHER PUBLICATIONS

Omidian et al., "Elastic, Superporous Hydrogel Hybrids of Polyacrylamide and Sodium Alginate", Macromolecular Bioscience, Sep. 15, 2006, pp. 703-710, vol. 6(9). Wiley-VCH, Weinheim.

(Continued)

*Primary Examiner* — Paul Dickinson
(74) *Attorney, Agent, or Firm* — Peter A. Nieves; Sheehan Phinney Bass & Green PA

(57) ABSTRACT

Method for making a tough and compliant hydrogel. A precursor hydrogel is made of a first polymer selected to maintain high elasticity and a second polymer selected to dissipate mechanical energy. The precursor hydrogel is stretched to a multiple of its original length to form a pre-stretched hydrogel. The pre-stretched hydrogel is allowed to relax and is soaked in a biocompatible solvent to reach equilibrium swelling of the pre-stretched hydrogel whereby shear modulus of the hydrogel is reduced.

4 Claims, 3 Drawing Sheets

(56) References Cited

OTHER PUBLICATIONS

He et al., "Tough and super-resilient hydrogels synthesized by using peroxidized polymer chains as polyfunctional initiating and cross-linking centers", Soft Matter, Jan. 24, 2013, p. 2837, vol. 9. RSC Publishing, London.

Tang et al., "Fabrication of a high-strength hydrogel with an interpenetrating network structure", Colloids and Surfaces A: Physicochemical and Engineering Aspects, Jun. 9, 2009, pp. 91-98. vol. 346(1-3), Elsevier B.V., Amsterdam.

Notification of Transmittal of the International Search Report and the Written Opinion for PCT/US2015/068981 dated May 17, 2016.

Lin et al., "Designing Extremely Resilient and Tough Hydrogels via Delayed Dissipation", Extreme Mecanics Letters, 2014, pp. 70-75, vol. 1, Elsevier Ltd., US.

COMPLIANT YET TOUGH HYDROGEL SYSTEMS AS ULTRASOUND TRANSMISSION AGENTS

This application claims priority to U.S. provisional application Ser. No. 62/095,243 filed on Dec. 22, 2014, the contents of which are incorporated herein by reference.

This invention was made with government support under grant number N00014-14-1-0619 awarded by the Office of Naval Research. The government has certain rights in the invention.

BACKGROUND OF THE INVENTION

This invention relates to a method for making a tough and compliant hydrogel with a low shear modulus that is extremely tough and robust.

It is desirable to have hydrogels be both resilient and tough. A particular use for such a hydrogel is as a transmission agent for ultrasound because resiliency allows it to conform to a body part. Resilience and toughness appear to be intrinsically contradictory properties but can be achieved according to the methods disclosed herein.

SUMMARY OF THE INVENTION

The method for making a tough and compliant hydrogel according to the invention includes combining a long chain polymer network to maintain high elasticity and a sacrificial chain polymer network to dissipate mechanical energy to form an interpenetrating hydrogel. The interpenetrating hydrogel is prestretched to a prescribed multiple of its original length and then relaxed for multiple cycles. Thereafter, the pre-stretched hydrogel is soaked in a biocompatible medium to reach equilibrium swelling of the hydrogel. As a result, the shear modulus of the hydrogel is significantly reduced. To achieve extremely low modulus, multiple loading-unloading steps are performed to deplete most of the sacrificial polymer network to a controlled degree.

The long chain network may be selected from a group consisting of polyacrylamide, polyethylene glycol, poly (vinyl alcohol), poly (N-isopropyl acrylamide), and poly (2-hydroxyethyl methacrylate). The sacrificial chain network may be selected from the group consisting of alginate, hyaluronic acid, collagen, agarose, gelatin, fibrin and chitosan. The hydrogel made by the method of the invention may be used as an ultrasound transmission agent.

DESCRIPTION OF THE PREFERRED EMBODIMENT

Figure 1:
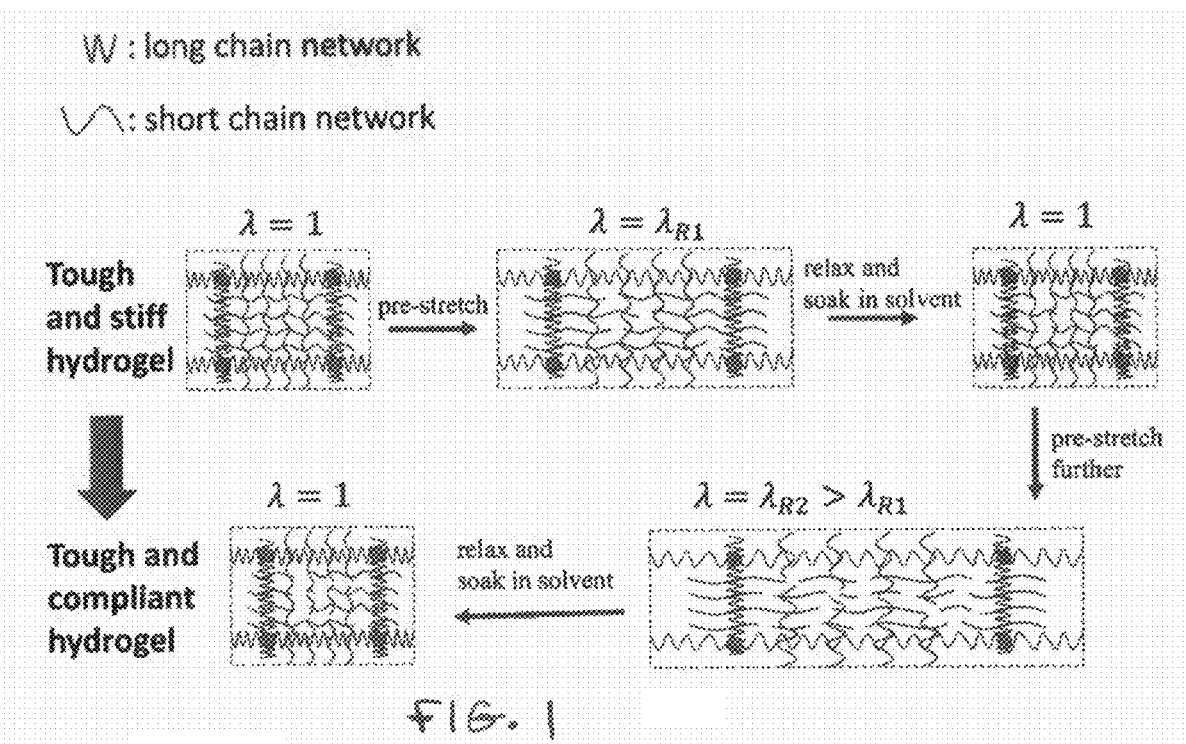
FIG. 1 is a schematic illustration of the steps performed according to the invention to transform a tough and stiff hydrogel into a tough and compliant hydrogel by pre-stretching the gel, relaxing and soaking it in a solvent such media or PBS.

We have invented a method and material system to make new hydrogels that have a shear modulus as low as 1 kPa but are extremely tough and robust. The extraordinary properties of the hydrogels are achieved through the mechanisms of delayed stiffening and mechanical dissipation. The hydrogels of the invention can be formed and printed into various shapes with different dimensions. As a result of their low rigidity and high robustness, the gels of the invention can be conformally attached to different regions of the human body. This aspect is important when the novel gel system of the invention is used as an ultrasound transmission agent.

In general, materials from which the hydrogels are made according to the invention are from two types of polymers. One type of polymer maintains high elasticity of the hydrogel and the other type of polymer dissipates mechanical energy when the hydrogel is deformed. The first type of polymers include polyacrylamide, polyethylene glycol, poly (vinyl alcohol), poly (N-isopropyl acrylamide), and poly (2-hydroxyethyl methacrylate). The second type of polymers include alginate, hyaluronic acid, collagen, agarose, gelatin, fibrin, and chitosan, which are generally capable of reversible crosslinking.

The first type of polymers are usually crosslinked by methods including free-radical polymerization, UV crosslinking, gamma irradiation, electron beam irradiation and freeze thawing. The second type of polymers are usually crosslinked by methods including adding multivalent ions, changing ambient temperature and varying pH of the solution. The chain length between two adjacent crosslinkings of the first type polymers is generally much longer than that of the second type polymers. In addition, the volume concentration of the first type of polymers in the hydrogel can range from 5% to 40%, and that of the second type is usually lower than the first type, ranging from 0.15% to 10%. Therefore, the crosslinking density of the second type polymers is usually much larger than the first type polymers. The possible combination of different polymers to form tough hydrogels are summarized in the matrix shown in Table 1.

TABLE 1

Tough hydrogels are fabricated by combining two types of polymer networks with different concentrations and crosslinking densities. A matrix is used to guide the selection of different polymers.

| Network for maintaining elasticity (long chain) | Network for dissipating energy (short chain) | | | | | | |
|---|---|---|---|---|---|---|---|
| | Alginate | Hyaluronic acid | Collagen, | Agarose | Gelatin | Fibrin | Chitosan |
| Polyacrylamide | | | | | | | |
| Polyethylene glycol | | | | | | | |
| Poly (vinyl alcohol) | | | | | | | |
| Poly(N-isopropylacrylamide) | | | | | | | |
| Poly(2-hydroxyethyl methacrylate) | | | | | | | |

An example protocol for making a specific hydrogel with polyacrylamide and alginate is now described. A pre-gel solution was prepared by mixing alginate (Sigma, A20330) and acrylamide (sigma, A8887) into a solution with one to five weight percent of alginate and 5-40 weight percent, of acrylamide. We then added N,N-methylenebisacryiamide (Sigma, 146072) as the crosslinker for polyacrylamide and ammonium persulphate (Sigma, 248614) as photo initiator for polyacrylamide. The concentration of the N,N-meihylenebisaerylamide needs to be very low (i.e., less than $4 \times 10^{-4}$ g per 10 ml of the polymer solution) to enable the low modulus of the hydrogels in fixture steps. After degassing the pre-gel solution in a vacuum chamber, we added calcium sulfate (Sigma, C3771) as the crosslinker for alginate and N,N,N'N'-tetramethylethyienediamine (Sigma, T7024-50M) as the crosslinking accelerator for polyacrylamide. Thereafter, the pre-gel solution was infused into molds of different shapes and was subjected to ultraviolet, light for 60 minutes wife 8 W power and 254 nm wavelength to fabricate the initial hydrogel.

Figure 2:
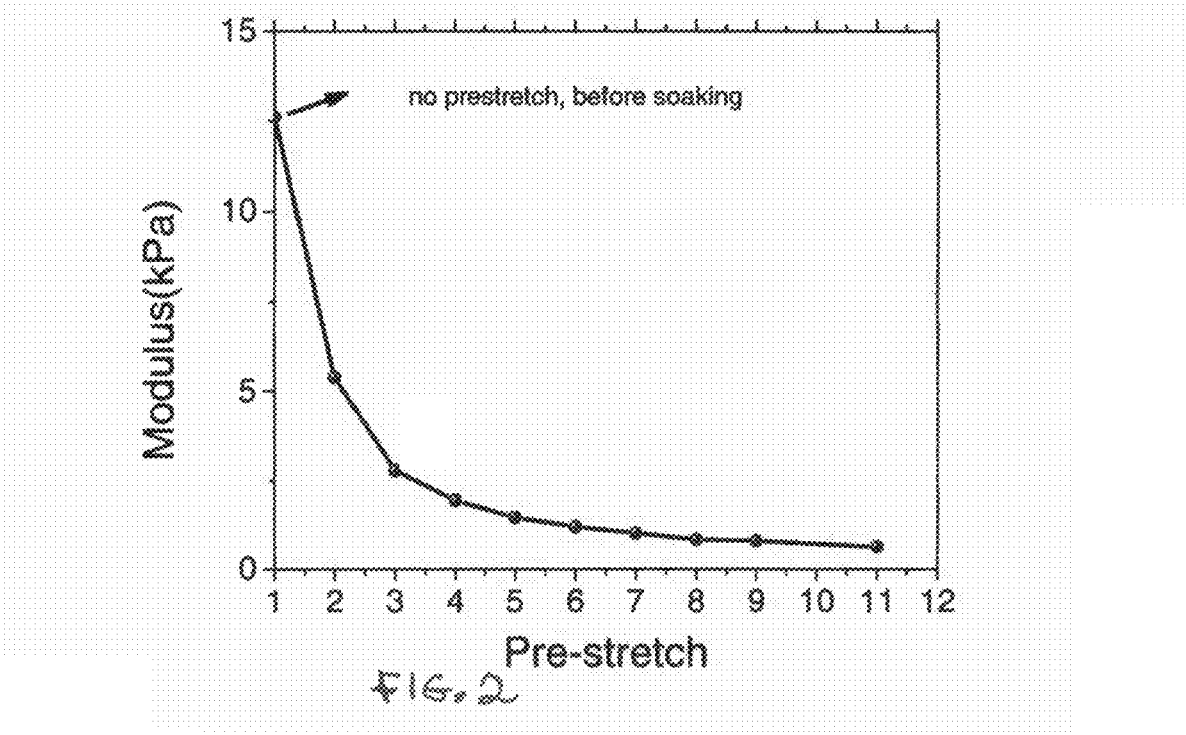
FIG. 2 is a graph of modulus against pre-stretch. One can see that soaking the pre-stretched hydrogel in solvent can significantly reduce the shear modulus of the hydrogel from over 10 kPa to approximately 1 kPa.
Figure 3:
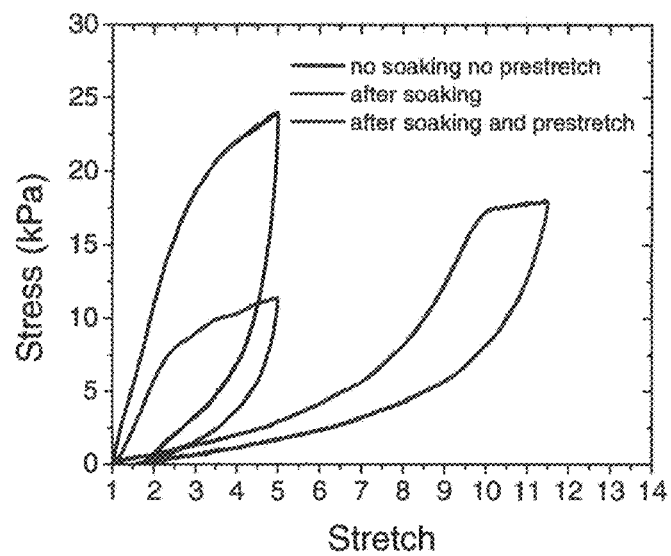
FIG. 3 is a comparison graph of stress versus stretch for hydrogels with different treatments.

The as-fabricated pre-gel hydrogels are relatively stiff with a shear modulus over 10 kPa and up to 100 kPa as shown in FIG. 2. The inventors have developed an innovative and practical method to reduce the modulus of the hydrogel while maintaining its high fracture toughness. With reference first to FIG. 1, we first pre-stretch the hydrogel for a prescribed time to a multiple of its original length (i.e., $\lambda_{r1}=2\sim10$) and then relax for multiple cycles. We then soak the pre-stretched hydrogel in a biocompatible solvent such as PBS or media over a period of time to reach equilibrium swelling of the hydrogel. We then stretched the hydrogel again to a ratio higher than the first pre-stretch (i.e., $\lambda_{r2}>\lambda_{r1}$) and then relax for multiple cycles. As a result, the shear modulus of the hydrogel will be significantly reduced as shown in FIG. 2. For example, when the ratio of the second stretch $\lambda_{r2}>7$, the shear modulus of the hydrogel is reduced to approximately 1 kPa. Although the resultant hydrogel has a very low shear modulus, it is still very tough as indicated by the stress versus strain curve of the hydrogel under loading and unloading. With reference to FIG. 3 it can be seen that the pre-stretched and soaked hydrogel still provides very high stretchability (over 11 times) and significant mechanical dissipation indicated by the hysteresis loop. The combination of high stretchability and mechanical dissipation give high fracture toughness to the resulting compliant hydrogel.

Figure 4A:
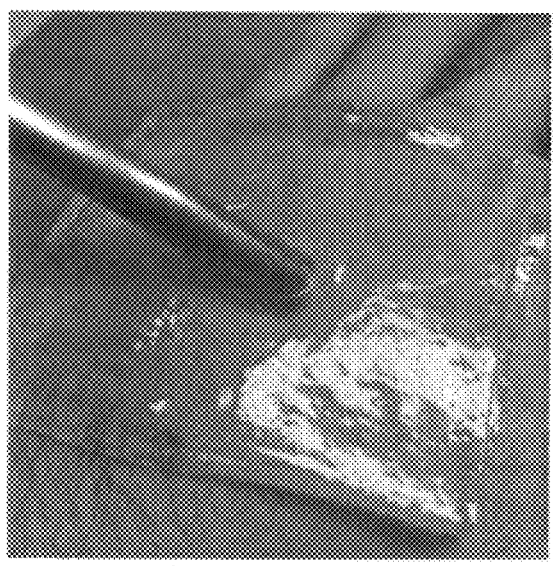
FIGS. 4a and 4b are photographs of the soft and tough hydrogel of the invention conformably attached to different regions of a human body.
Figure 4B:
Figure 5A:
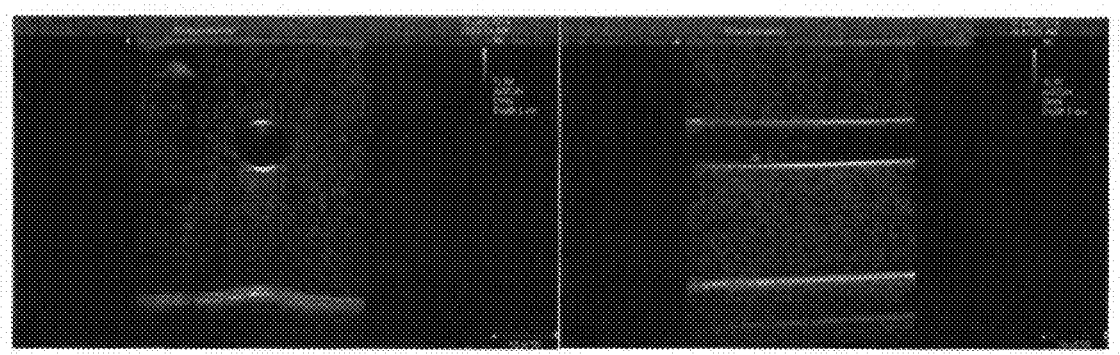
FIGS. 5a and 5b are ultrasound images of a phantom object measured through conventional liquid hydrogel as shown in FIG. 5a and the extremely compliant and tough hydrogel of the invention shown in FIG. 5b.
Figure 5B:

As shown in FIGS. 4a and 4b, the extremely soft and tough hydrogel disclosed herein can be conformally attached to different regions of a human body. The material can also conformally deform and wrap around ultrasound probes of various shapes. In addition, because the hydrogel is elastic and extremely tough, it will not flow or fracture as commonly used ultrasound gels do. Furthermore, since the shear modulus of the hydrogel is very low (approximately 1 kPa), it is expected to give excellent transmission efficiency for ultrasound. As shown in FIGS. 5a and 5b, the extremely compliant and tough hydrogel of the invention gives high quality ultrasound images. However, whereas conventional liquid hydrogel flows away or dehydrates after approximately one minute of measurement, the novel compliant and tough hydrogel of the invention can last 30 minutes to hours.

Additional information concerning this invention may be found in Lin et al., "Designing Extremely Resilient and Tough Hydrogels via Delayed Dissipation", Extreme Mechanics Letters 1 (2014) 70-75. Reference may also be made to international publication number WO2013/103956. The contents of both of these references are incorporated herein by reference.

It is recognized that modifications and variations of the invention will be apparent to those of ordinary skill in the art and it is intended that all such modifications and variations be included within the scope of the appended claims.

What is claimed is:

1. Method for making a tough and compliant hydrogel comprising:
   combining a polymer network selected to maintain elasticity and a sacrificial chain polymer network to dissipate mechanical energy to form an interpenetrating hydrogel;
   stretching the interpenetrating hydrogel a first time to a first multiple of its original length to form a pre-stretched hydrogel;
   allowing the pre-stretched hydrogel to relax;
   soaking the relaxed hydrogel in a biocompatible solvent to reach equilibrium swelling of the hydrogel; and
   stretching the interpenetrating hydrogel a second time to a second multiple of its original length wherein the second multiple is greater than the first multiple, whereby shear modulus of the hydrogel is reduced.

2. The method of claim 1 wherein the multiple of its original length is in the range of 2-10.

3. The method of claim 1 wherein the polymer network is selected from the group consisting of polyacrylamide, polyethylene glycol, poly (vinyl alcohol), poly (N-isopropyl acrylamide), and poly (2-hydroxyethylmethacrylate).

4. The method of claim 1 wherein the sacrificial chain polymer network is selected from the group consisting of alginate, hyaluronic acid, collagen, agarose, gelatin, fibrin and chitosan.

* * * * *